US006227197B1

United States Patent
Fitzgerald

(10) Patent No.: US 6,227,197 B1
(45) Date of Patent: *May 8, 2001

(54) GAS SUPPLYING AND SUBSTANCE SUCTIONING RELATIVE TO A PATIENTS TRACHEA

(75) Inventor: Peter M. Fitzgerald, Parker, CO (US)

(73) Assignee: Respironics, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/477,986

(22) Filed: Jan. 5, 2000

Related U.S. Application Data

(63) Continuation of application No. 08/988,605, filed on Dec. 10, 1997.

(51) Int. Cl.[7] .................................................. A61M 16/00
(52) U.S. Cl. .............................. 128/200.26; 128/207.14; 128/207.16; 128/912
(58) Field of Search .................... 128/200.26, 207.14, 128/207.15, 207.16, 912, DIG. 26

(56) References Cited

U.S. PATENT DOCUMENTS

| | | | |
|---|---|---|---|
| 3,945,378 | 3/1976 | Paluch | 128/145.8 |
| 3,991,762 | 11/1976 | Radford | 128/276 |
| 4,036,210 | * 7/1977 | Campbell et al. | 128/2 F |
| 4,193,406 | 3/1980 | Jinotti | 128/204.18 |
| 4,291,691 | 9/1981 | Cabal et al. | 128/204.18 |
| 4,569,347 | 2/1986 | Frisbie | 128/344 |
| 4,836,199 | 6/1989 | Palmer | 128/207.16 |
| 4,872,579 | * 10/1989 | Palmer | 128/205.19 |
| 4,887,997 | 12/1989 | Okada | 604/54 |
| 4,967,743 | * 11/1990 | Lambert | 128/202.16 |
| 5,088,486 | 2/1992 | Jinotti | 128/207.14 |
| 5,101,813 | 4/1992 | Trick | 600/40 |
| 5,140,983 | 8/1992 | Jinotti | 128/207.14 |
| 5,254,097 | 10/1993 | Schock et al. | 604/167 |
| 5,277,177 | 1/1994 | Page et al. | 128/200.26 |
| 5,309,902 | * 5/1994 | Kee et al. | 128/207.16 |
| 5,309,906 | 5/1994 | LaBombard | 128/207.14 |
| 5,368,017 | * 11/1994 | Sorenson et al. | 128/200.26 |
| 5,405,341 | 4/1995 | Martin | 604/284 |
| 5,419,314 | 5/1995 | Christopher | 128/200.26 |
| 5,642,726 | * 7/1997 | Owens et al. | 128/200.26 |
| 5,694,929 | 12/1997 | Christopher | 128/207.14 |
| 5,713,849 | 2/1998 | Bosma et al. | 604/28 |
| 5,730,123 | * 3/1998 | Lorenzen et al. | 128/207.14 |
| 5,735,271 | * 4/1998 | Lorenzen et al. | 128/207.16 |
| 5,738,091 | 4/1998 | Kee et al. | 128/205.12 |

(List continued on next page.)

FOREIGN PATENT DOCUMENTS

| | | |
|---|---|---|
| 9321981 | 11/1993 | (WO) . |
| WO 93/21981 | 11/1993 | (WO) . |
| 9531250 | 11/1995 | (WO) . |
| WO 95/31250 | 11/1995 | (WO) . |
| 9626757 | 9/1996 | (WO) . |
| WO 96/26757 | 9/1996 | (WO) . |

Primary Examiner—Aaron J. Lewis
(74) Attorney, Agent, or Firm—Michael W. Haas

(57) ABSTRACT

A gas insufflation and suction apparatus is provided for communication with a patient's trachea. The apparatus includes a gas catheter and a suction catheter. When supplying a suitable gas having a desired oxygen concentration to the patient, an output end of the gas catheter is moved past a Y-connector through a T-member into the patient's trachea. After removal of the gas catheter from the patient's trachea, mucus or other substances can be removed from the patient using the suction catheter. With the gas catheter in its standby position, the suction catheter is moved past the Y-connector through the T-member and located in a desired position in the patient's trachea.

14 Claims, 3 Drawing Sheets

U.S. PATENT DOCUMENTS

| | | | |
|---|---|---|---|
| 5,752,921 | 5/1998 | Orr | 600/533 |
| 5,788,680 | 8/1998 | Linder | 604/280 |
| 5,791,337 | 8/1998 | Coles et al. | 128/200.26 |
| 5,803,078 * | 9/1998 | Brauner | 128/912 |
| 5,813,402 * | 9/1998 | Jinotti | 128/912 |
| 5,823,184 * | 10/1998 | Gross | 128/912 |
| 5,836,918 | 11/1998 | Dondlinger | 604/171 |
| 6,012,451 * | 1/2000 | Palmer | 128/200.26 |

* cited by examiner

GAS SUPPLYING AND SUBSTANCE SUCTIONING RELATIVE TO A PATIENTS TRACHEA

This application is a cont. of Ser. No. 08/988,605, filed Dec. 10, 1997.

FIELD OF THE INVENTION

The present invention relates to medical catheters and, in particular, to apparatus and method for selectively ventilating and suctioning a patient using two separate catheters.

BACKGROUND OF THE INVENTION

Delivery of oxygen to a patient using a catheter positioned within an endotracheal tube is a well-established medical procedure. The oxygen is provided to assist in maintaining adequate oxygenation and ventilation. The catheter carries the oxygen in a suitable concentration directly into the distal trachea, 2–3 cm from the carina, bypassing the upper airways. This is intended to be accomplished while avoiding ventilator-induced complications.

Patients suffering from severe respiratory or ventilatory distress are sometimes recipients of this procedure commonly known in the medical literature as Thoracic Gas Insufflation (TGI) procedures. Major steps associated with such a procedure include positioning a catheter at a predetermined location in the patient's trachea and then causing oxygen to be delivered at a desired concentration. Commonly, mucous or other substances must be removed from the patient on a periodic basis. In accordance with one known medical device and procedure, a single catheter is alternately used to first deliver a ventilating oxygen/air mixture and then used to remove substances from the patient. This single catheter is inserted into the trachea of the patient. Under operator or technician control, a selection is made to either (1) deliver an oxygen/air mixture or (2) suction unwanted substances from the patient. Oxygen/air mixture delivery and patient suctioning procedures are then alternated using the same catheter. This device is also known to maintain sterility of its single catheter by means of a collapsible bag that surrounds the single catheter and prevents unwanted exposure to the environment. However, this device utilizes a single catheter whose diameter (french size) is less than ideal for either purpose. Typically, the catheter is too large in diameter for optimal oxygen/air mixture delivery within an endotracheal tube and too small in diameter for optimal efficiency in removing unwanted substances. In the other known method, two separate and different size catheters are used. One catheter for delivering the oxygen/air mixture and another catheter for removing unwanted substances from the patient's trachea. Although each catheter may be ideally sized for its intended purpose, there is no unitary and convenient mechanism that facilitates the performing of these two functions and procedures.

SUMMARY OF THE INVENTION

In accordance with the present invention, an apparatus is provided for selectively supplying a gas including an oxygen/air mixture to a patient and for suctioning mucous or other substances from the patient. The apparatus includes a tracheal gas assembly that includes a gas catheter for carrying gas having a desired composition including a suitable concentration of oxygen to the patient. A first or gas catheter enclosure member surrounds substantial portions of the gas catheter when it is not being utilized to supply gas, to the patient's body passageway, such as the trachea. A holding or clamp member surrounds a portion of the gas catheter and is used to hold or fix the gas catheter in a desired or predetermined position relative to the trachea of the patient. Adjacent to an output end of the gas catheter, when the gas catheter is in a standby position and not being utilized to carry gas to the patient, a first or gas catheter indicator element is located or otherwise provided to indicate to the practitioner that the gas catheter is in its standby position. The gas catheter also has a continuous series of numerically labeled location markers positioned 2 cm apart beginning 10 cm from the gas catheter's output end and proceeding proximally along the gas catheter's body ending at the 42 cm. mark. These location markers enable the practitioner or operator to identify the position of the extended gas catheter's output end relative to the endotracheal tube in the patient's trachea. The gas catheter also has a radio opaque stripe running along its entire body length so that the practitioner or operator can also determine or verify the exact position of the gas catheter in the patient's trachea through the use of a chest x-ray.

The apparatus further includes a suction assembly having a second or suction catheter that is separate and detached from the gas catheter. The suction catheter is used to remove mucous or other substances from the patient when its input end is suitably located within the patient's trachea or other body passageway. Like the gas catheter, the suction catheter has substantial portions surrounded by a second or suction catheter enclosure member when the suction catheter is removed from the patient's trachea or other body passageway and is in its standby position. When the suction catheter is in its standby position, the gas catheter can be advanced and properly located in the patient's trachea. Likewise, when the gas catheter is in its standby position, the suction catheter can be advanced and properly located in the patient's trachea. The suction catheter also has a catheter position indicator element formed or otherwise provided adjacent to its input end. The suction catheter position indicator element is used to provide an indication to the practitioner or operator when the suction catheter is in its standby position.

The apparatus also includes a common or Y-connector having first and second legs. The gas catheter is able to move within and relative to the first leg and with one end of the first enclosure member being held adjacent to the first leg. Similarly, the suction catheter is able to move within and relative to the second leg. The Y-connector has a common section that communicates with each of the two legs. When the gas catheter is located within the patient's trachea, portions of the gas catheter occupy space in the common section. When the suction catheter is located within the patient's trachea, portions of the suction catheter occupy space in the common section.

The apparatus also includes a connector unit that is joined to or operatively associated with the Y-connector. The connector unit includes a T-member having a connector tube or member that is used to connect or join the Y-connector to the T-member. The T-member also has a short connector on the opposite side of the main tube that connects to the patient's endotracheal tube while fluidly communicating with the T-member's main tube and joined Y-connector. When being used, the selected catheter, either the gas catheter or the suction catheter is advanced within the Y-connector, the T-member connector tube, across the main tube of the T-member through the short connector into the patient's endotracheal tube and then into the patient's trachea. The T-member's main tube also preferably has a magnifying section or element to facilitate visual recognition of a numerically labeled location markers positioned 2 cm apart beginning 10 cm from the distal tip and proceeding approximately to the 42 cm mark along the body of the catheter. The numerically labeled location markers are identically positioned on the body of both the gas catheter and the suction catheter. Such location markers, when positioned within the T-member main tube and under the magnifying element, can assist the practitioner or operator in properly positioning either of the two catheters relative to the patient's trachea. The T-member main tube will also preferably include a first swivel connector through which the entire tracheal gas assembly is operatively attached to the patient's endotracheal tube. The T-member main tube will also preferably include a second swivel connector to which a primary source of inspiratory gas and ventilatory assistance is operatively attached.

With regard to methods of operation, the apparatus of the present invention has communication with the trachea of the patient by means of the endotracheal tube located in the patient's trachea. Subsequently, for supplying a ventilating gas to the patient, which also includes a desired concentration of oxygen, the gas catheter is manipulated or caused to move by the practitioner by engagement thereof while contacting the collapsible first enclosure member. The output end of the gas catheter is moved past the first leg of the Y-connector through the connector member of the T-member, through the main tube of the T-member and through the short connector for proper positioning in the patient's trachea. Such a proper position is determinable using the first or gas catheter marker on the gas catheter and the magnifying element on the main tube of the T-member. Gas can then be supplied to the patient through the gas catheter. Once the gas catheter is properly positioned in the patient's trachea, the clamp member is turned, moved or otherwise controlled to engage the gas catheter for holding it against inadvertent movement.

When it is desired to remove unwanted substances from the patient's trachea, the gas catheter must be removed and pulled in the opposite direction by engaging the gas catheter through contact with the first enclosure member. The output end of the gas catheter is thereby pulled back through the T-member and into the Y-connector, preferably, until the catheter position indicator element on the gas catheter is visible to the practitioner or operator in a position within the gas catheter enclosure member adjacent to the clamp member. With the catheter position indicator element on the gas catheter being visible at this location, the gas catheter is in its standby position. Once the gas catheter is in its standby position, the suction catheter can be advanced so that its input end passes through the common section of the Y-connector, and into the T-member by means of the connector member. The input end of the suction catheter is further advanced through the main tube and short connector and continues on until the suction catheter is properly located in the patient's trachea. At this time, a suction control member operatively connected to the suction catheter is engaged providing suction for the removal of mucus and other substances from the patient 's trachea.

Once the suctioning procedure or operation is performed, the suction catheter can then be removed from the patient's trachea and located in its standby position relying on the second or suction catheter position indicator element provided with the suction catheter. Then, if desired or appropriate, the gas catheter can again be moved from its standby position into the patient's trachea.

Based on the foregoing summary, a number of advantages of the present invention are readily seen. A unitary apparatus is provided for desired positioning of a selected one of a gas catheter and a suction catheter in a patient's trachea. The apparatus is characterized by a common or Y-connector, which enables each of the two catheters to be separately and selectively located in the patient's trachea. Alternating uses of the gas catheter and the suction catheter can be employed, while appropriate sterility of the catheters is maintained. Either the gas or suction catheters is easily moved into and removed from a proper position within the patient's trachea. However, the two catheters are never positioned in the patient's trachea at the same time. Accordingly, the suction catheter, which typically has a size of 14 french (fr.), and the gas catheter, which typically has a size of 8–10 fr., are never occupying space inside the patient's trachea at the same time. Once in the proper position relative to the patient's trachea for supplying the ventilating gas, the gas catheter is held in place against inadvertent movement by means of a readily manipulated clamp member. Each of the gas and suction catheters also has a catheter position indicator element that can be observed to inform the practitioner or operator regarding the standby positions of these two catheters. When in the standby positions, a selected catheter can be advanced into the trachea of the patient without interference or obstruction from the other catheter.

Additional advantages of the present invention will become readily apparent from the following discussion, particular when taken together with the accompanying drawings.

DETAILED DESCRIPTION

Figure 1:
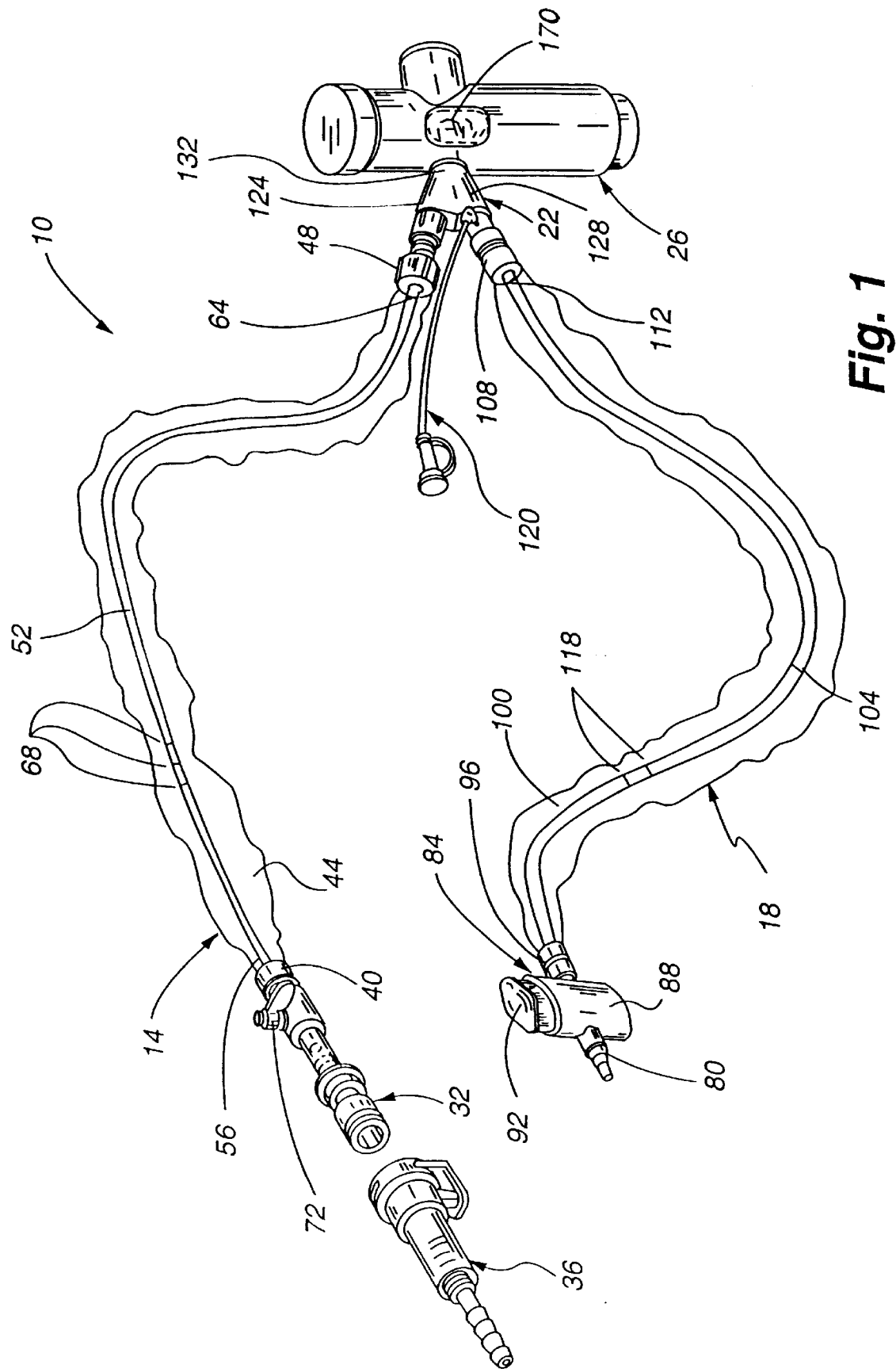
FIG. 1 is a perspective view of the apparatus illustrating the separate and detached gas and suction catheters including being received by the common or Y-connector.

With reference to FIG. 1, an apparatus 10 is illustrated for supplying gas having a desired or appropriate concentration of oxygen to the patient's trachea. The apparatus 10 is also used to suction mucus or other unwanted substances from the patient's trachea. The apparatus 10 includes a tracheal gas assembly 14 used in the delivery of the gas, a suction assembly 18 used to remove mucus and other unwanted substances from the patient's trachea, a common or Y-connector 22 that holds or otherwise engages portions of the tracheal gas assembly 14 and the suction assembly 18, and a connector unit 26 to which the Y-connector 22 is joined. The connector unit 26 outputs the gas supplied by the tracheal gas assembly 14, as well as acting as a conduit to a ventilator that is providing oxygenation and ventilation for the patient.

The tracheal gas assembly 14 includes an input member 32 that communicates with a source of gas, i.e., gas to be supplied to the patient's trachea. The input member 32 is located at one end of the tracheal gas assembly 14. In one embodiment, an adaptor member 36 is joined to the input member 32 for adapting the tracheal gas assembly 14 for connection to an oxygen hose from an oxygen source. In another embodiment, input member 32 is connected directly to a heated wire circuit from a heat and humidification device that heats and humidifies the gas being supplied to the patient's trachea. A gas fixture 40 is connected to the input member 32 and receives a first or gas catheter enclosure member 44. More specifically, the gas fixture 40 is cylindrical in shape, and its inner sidewall holds the enclosure member 44 at its distal end relative to the Y-connector. The first enclosure member 44 has its proximal end (adjacent to the Y-connector 22) joined at a clamp or holding member 48. Contained within and surrounded by the first enclosure member 44 is a gas catheter 52 having an input end 56, which is adjacent to the gas fixture member 40 and an output end 60 (FIG. 2) for outputting the tracheal gas to the patient. The first enclosure member 44, as is well known, acts to prevent access or communication with the surrounding environment to maintain desired sterility of the gas catheter 52, as will be important and explained in conjunction with the operation or process steps involving the apparatus 10 including gas catheter 52. In one embodiment, the size of the gas catheter is 8 fr., but may vary between 8–10 fr. The gas catheter 52 may include a single port at its end, or, alternatively, may have one or more side ports as well as the port at its end. In another embodiment, the single end port may have a bend adjacent thereto and thereby provide a J-configuration at its end.

The gas catheter 52 also includes a first or gas catheter position indicator element 64 formed or otherwise provided adjacent to the output end 60 of the gas catheter 52. The first catheter position indicator element 64 can be a small area of different color on the outside wall or surface of the gas catheter 52. The first catheter position indicator element 64 is useful in informing the practitioner or operator that the gas catheter 52 is in its standby (home) position. The standby position means or refers to that position of the gas catheter 52 that permits the suction catheter assembly 18 to be utilized for its suctioning purposes, as will also be explained later in more detail. The gas catheter 52 also has numerically labeled location markers 68, positioned 2 cm apart, starting 10 cm from the output end 60 and continuing proximally along the gas catheter to the 42 cm mark. The numerically labeled location markers are also typically formed or otherwise provided on the outer wall of the gas catheter 52 and are readily differentiable from other sections of the gas catheter 52 by color or other indicator. The numerically labeled location markers 68 are used by the practitioner to determine the position of the gas catheter 52 relative to the patient's trachea. More specifically, (when) the practitioner or operator advances the gas catheter 52 into the patient's trachea until a predetermined numerally labeled location marker is visible in the magnifier 170 located on the main tube 140, and the practitioner is notified that the output end 60 of the gas catheter is properly positioned within the patient's trachea. The gas catheter also has a radio opaque stripe along the entire length of its body. This radio opaque stripe enables the practitioner or operator to determine or verify the exact location of the gas catheter 52 in the patient's trachea via chest x-ray.

The gas assembly 14 also includes an auxiliary gas port 72. This port 72 is provided adjacent to the gas fixture member 40 and joined to the gas input member 32. The auxiliary gas port 72 offers an entry way for potentially adding other gases, e.g., nitric oxide, to the primary oxygen/air mixture being supplied to the patient's trachea. The auxiliary port 72 includes a cap or cover that closes off the entry way when not being used to supply another gas.

The suction assembly 18 has an input device 80 for communication with a source of negative pressure or vacuum to draw or suction when appropriate. The input device 80 is operatively connected to a suction control member 84 that includes a body 88 and a control element 92. Suction is activated by the practitioner or operator by depressing the control element 92.

The suction catheter assembly 18 also includes a distal suction fixture 96 to which a second enclosure member 100 is joined at one of its ends. The second enclosure member is equivalent to the first enclosure member 44 and surrounds or contains a suction catheter 104. The opposite end of the second enclosure member 100 is joined to a proximal suction fixture 108. The suction catheter 104 is greater in size or diameter than the gas catheter 52 and has a diameter of about 14 fr. Such a size is preferable in connection with removing mucus and other unwanted materials within the patient's trachea. Similar to the gas catheter 52, the suction catheter 104 includes a second or suction catheter position indicator element 112 adjacent to an input end 116 (FIG. 2) thereof. The second catheter position indicator element 112, when observable or outwardly of the proximal suction fixture 108, provides an indication to the practitioner or operator that the suction catheter 104 is in its standby position, which means that the gas catheter 52 can be advanced or positioned into the patient's trachea, as will be discussed further in conjunction with the operation of the apparatus 10. The suction catheter 104, like the gas catheter 52, also has numerically labeled location markers 118 that can be used by the practitioner or operator in connection with determining that the suction catheter 104 is in the necessary or appropriate position relative to the patient's trachea.

The suction assembly 18 also has, in one embodiment, a catheter rinse assembly 120, which is provided at the opposite end of the suction assembly 18 from the input device 80. The catheter rinse assembly 120 is useful in receiving liquid, such as a saline solution, for use in rinsing or flushing the suction catheter 104.

Figure 2:
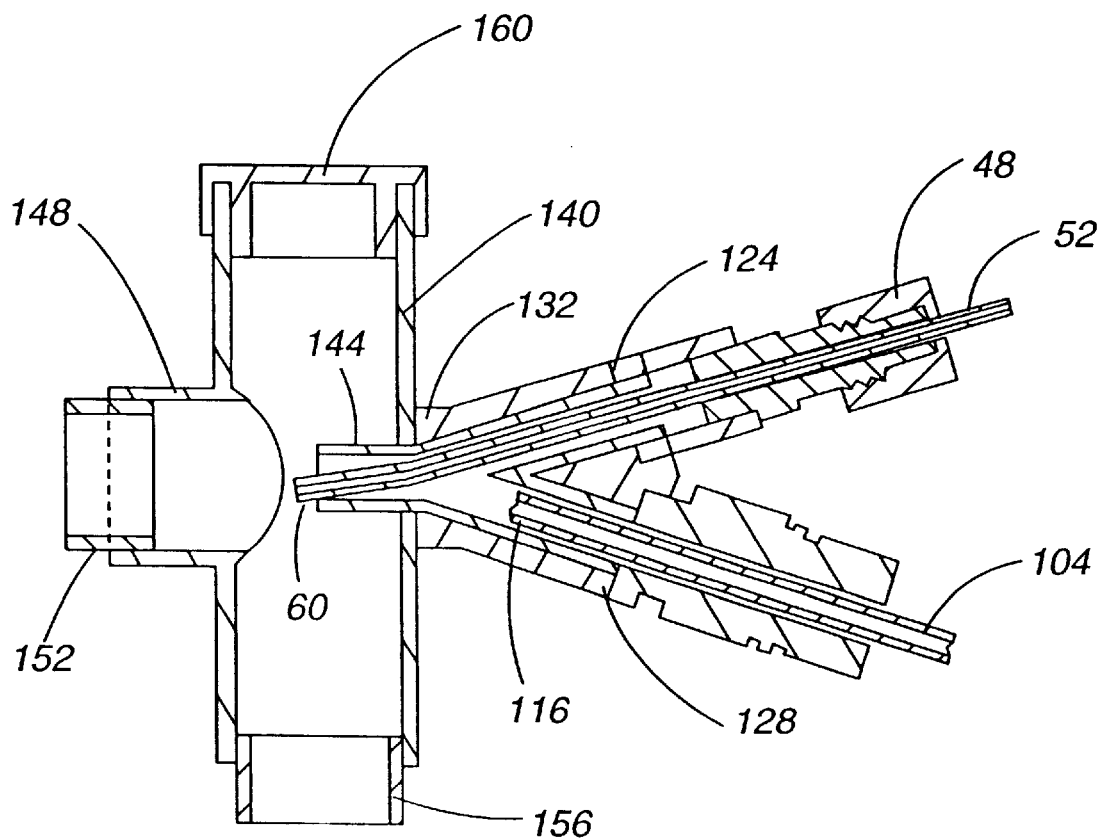
FIG. 2 is an enlarged, fragmentary, longitudinal cross-section illustrating the Y-connector and the suction and gas catheters, with the gas catheter advanced through the connector member of the T-member.

With regard to the common or Y-connector 22 and also with reference to FIG. 2, it includes a first or gas leg 124 and a second or suction leg 128. Each of these two legs 124, 128 converges to a common section 132. The first leg 124 receives the gas catheter 52 and the gas catheter 52 moves relative to the first leg 124. Similarly, the second leg 128 receives the suction catheter 104 and the suction catheter 104 is able to move relative to the second leg 128.

Figure 3:
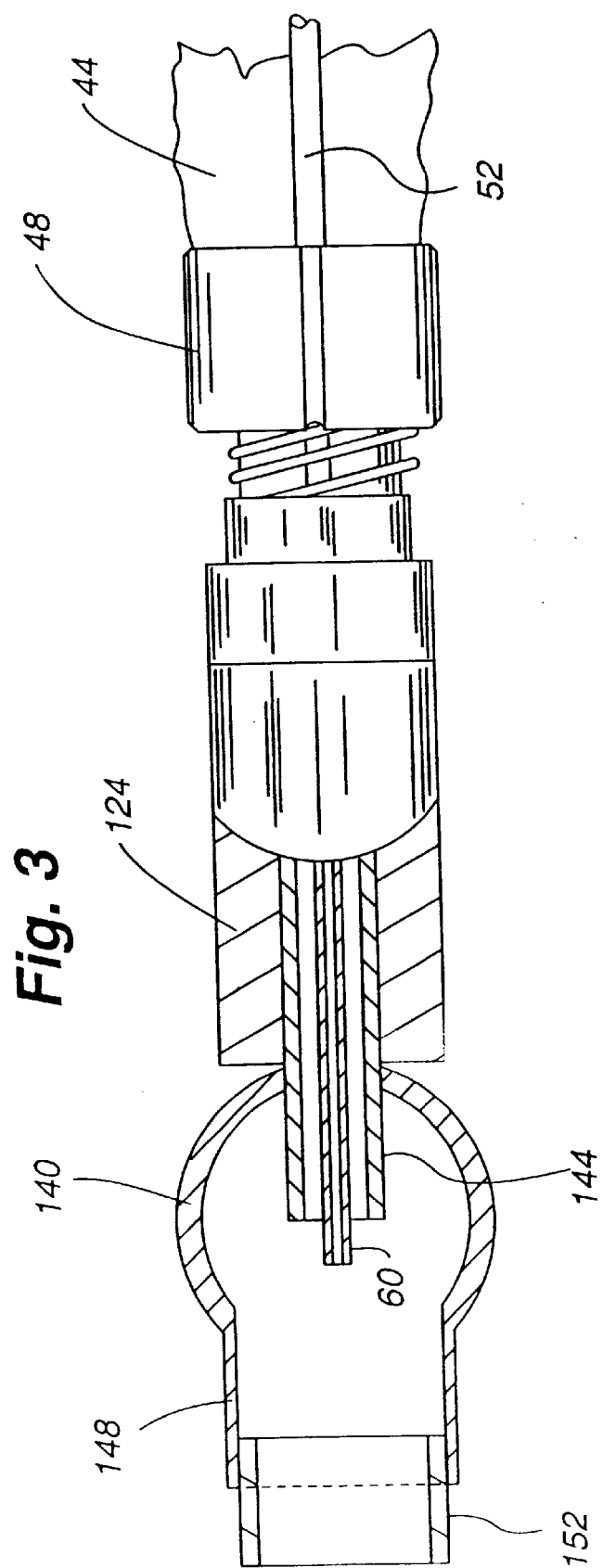
FIG. 3 is an enlarged, lateral, cross-sectional view illustrating an arrangement among the gas and suction catheters, the T-member, and the Y-connector when the gas catheter is located through the connector member of the T-member.

With reference to FIGS. 1–3, the connector unit 26 is next described in more detail. The connector unit 26 includes a main tube 140 that is joined to a number of separately definable connector or communication elements to define a T-member. These elements include a connector tube 144 that communicates with and connects to the common section 132 of the Y-connector 22. The connector tube 144 extends inwardly for some distance into the main tube 140, about halfway across the diameter of the main tube 140. The connector tube 144 has a diameter that is less than the combined diameters of the gas catheter 52 and the suction catheter 104 so that only one of these two catheters 52 and 104 is able to pass through the connector tube 144 at any one time. Preferably, the width or size of the common section 132 at its outlet end, where it joins with the connector tube 144, is also of a width or diameter that is less than the combined diameters of these two catheters 52 and 104. As seen in FIGS. 2 and 3, the input end 60 of the gas catheter 52 has been moved from its standby position past the common section 132 and through the connector tube 144. In this location, the input end 116 of suction catheter 104 is unable to pass through the connector tube 144 since it is blocked by portions of the gas catheter 52. The connector unit 26 also includes a short connector 148 that is formed integral with the main tube 140 and is located opposite of connector tube 144 and in position to readily receive the gas catheter 52 including its output end 60 as the gas catheter is advanced through the width or diameter of the main tube 140, after passing through the connector tube 144, and into this short connector 148. In the preferred embodiment, the short connector 148 has a first or swivel member 152 that allows for rotational movement. Typically, an endotracheal tube is connected to the first swivel member 152, while positioned within the trachea of the patient. The endotracheal tube is able to receive either the gas catheter 52 of the suction catheter 104, depending upon the medical procedure that is being conducted at the particular time. At the lower end of the main tube 140, a second swivel member 156 is provided to allow for rotational movement. Typically, the second swivel member 156 is connected to a ventilator circuit. The application and control of a ventilator and its circuit tp provide inspiratory gas to the main tube 140 is a well established procedure. The connector unit 26 also has a cap member 160 that provides a closed system for delivery of the insufflation gas and for the suctioning process.

The main tube 140, in one embodiment, is a substantially transparent, plastic member. Such a configuration enables the practitioner or operator to observe the selected numerically labeled location marker 68 or 118, whichever is presently being used and positioned within the patient's trachea. In that regard as well, in the preferred embodiment, the main tube 140, as schematically represented in FIG. 1, has a magnifier element 170 that magnifies or enlarges that which is viewed within the main tube 140 and disposed below the magnifying element 170. This facilitates the observation of the selected numerically labeled location markers 68 and 118.

The discussion of the present invention is continued in the context of the operation of the apparatus 10. Assume, for example, that both the gas catheter 52 and the suction catheter 104 are in their standby position as depicted in FIG. 1. Subsequently, it is desired that the gas catheter 52 be utilized to supply a ventilating gas to the patient's trachea. To accomplish this, the operator manipulates or advances the gas catheter 52 by engaging it through contact with the first enclosure member 44. In that regard, the output end 60 of the gas catheter 52 is pushed through the first leg 124 and the common section 132 of the Y-connector 22 and then past the connector tube 144. The gas catheter 52 continues to be advanced so that the output end 60 moves into and through the short connector 148. After passing through the short connector 148, the gas catheter 52 is further advanced into and through the patient's endotracheal tube and positioned within the patient's trachea. This proper position is made to or recognized by the practitioner or operator by means of the numerically labeled location markers 68 along the body of the gas catheter 52, that carries or acts as a conduit for this gas. When the gas catheter 52 is positioned within the patient's trachea, the clamp member 48 is rotated to hold the gas catheter 52 in the desired position. More specifically, the clamp member 48 is configured to fixedly engage portions of the first enclosure member 44 and the gas catheter 52 when the clamp member 48 is in a first or tightened position. In this position, the gas catheter 52 is immovable, even when a moderate amount of pulling or pushing on the gas catheter 52 is applied. As a result, the gas catheter 52 remains in the desired position relative to the patient's trachea during the supplying of gas to the patient's trachea.

In conjunction with the operation of the suction assembly 18, suctioning of the patient is commonly required in order to remove unwanted substances, such as mucus, from the patient's trachea. In the case in which the gas catheter 52 is already in place within the patient's trachea, it first must be removed before initiating the process for removing such unwanted substances. The suction catheter 104 is separated and detached from the gas catheter 52 so that both catheters 52, 104 are not located within the trachea at the same time. Relatedly, at least the size or diameter of the connector tube 144 does not allow for both catheters 52 and 104 to be moved through the connector unit 26 at the same time into the patient's trachea. Thus, the practitioner or operator must remove the gas catheter 52 from the patient's trachea by pulling on portions of the tracheal gas assembly 14, such as portions of the first enclosure member 44 and the gas catheter 52 or gas fixture 40. The gas catheter 52 is caused to be pulled from the patient's trachea until it is in its standby position, as can be observed using the gas catheter position indicator element 64 that can be seen after the gas catheter 52 has been sufficiently pulled from the patient's trachea so that the gas catheter position indicator element 64 is located adjacent to the clamp member 48 within the first enclosure member 44.

Once the gas catheter 52 is in its standby position, as noted by observation of the gas catheter position indicator element 64, the suction catheter 104 can be advanced (moved or pushed) in a direction toward the patient's trachea by contact with the second enclosure member 100 and corresponding engagement with suction catheter 104. By causing this movement, the input end 116 of the suction catheter 104 advances past the second leg 128 of the Y-connector 22 and into common section 132 of the Y-connector 22 and then passes into and through the connector tube 144 of the connector unit 26. Continued advancement (movement) of the suction catheter 104 continues through the short connector 148 and then into and through the patient's endotracheal tube for subsequent positioning into the patient's trachea. Like the gas catheter 52, the suction catheter 104 continues to be moved until a predetermined numerically labeled location marker 118 is observed using the magnifying element 170, which indicates to the practitioner or operator that the suction catheter 104 is properly positioned within the patient's trachea. At this time, proper suctioning of unwanted substances can occur, provided that the suction control member 84 including control element 92 is properly engaged allowing such suction to occur.

Subsequent gas supplying steps using the tracheal gas assembly 14 and, alternately, the steps of suctioning the patient using the suction assembly 18, can be made when necessary or appropriate. For example, when ventilating gas is again to be supplied to the patient using the tracheal gas assembly 14 and with the suction catheter 104 in place within the patient's trachea, it first must be removed by pulling back on the suction assembly 18 using portions thereof. The retraction of the suction catheter 104 from the patient's trachea, eventually results in the second catheter position indicator element 112 on the suction catheter 104 being observed by the practitioner or operator adjacent to the proximal fixture member 108 through the second enclosure member 100. With the suction catheter in its standby position, the gas catheter 52 can then be manipulated, moved or advanced as previously described in connection with desired placement of the gas catheter output end 60 within the patient's trachea.

The foregoing discussion of the invention has been presented for the purposes of illustration and description. Further, the description is not intended to limit the invention to the form disclosed herein. Consequently, variation and modification commensurate with the above teachings, within the skill and knowledge of the relevant art, are within the scope of the present invention including, but not limited to, possibly using the disclosed apparatus for body passageways other than the trachea. The embodiments described hereinabove are further intended to explain the best modes presently known of practicing the invention and to enable others skilled in the art to utilize the invention as such, with other embodiments, and with the various modifications required by their particular applications or uses of the invention. It is intended that the appended claims be construed to include alternative embodiments to the extent permitted by the prior art.

What is claimed is:

1. An adapter assembly for connection to a proximal end of an endotracheal tube, comprising:
   a first multi-limb connector having a first connector portion adapted to be coupled to a ventilator, a second connector portion adapted to be connected to an endotracheal tube, and a third connector portion;
   a second multi-limb connector having a fourth connector portion adapted to be immovably coupled to the third connector portion of the first multi-limb connector; a fifth connector portion, and a sixth connector portion;
   a gas delivery catheter having a first diameter, wherein the gas delivery catheter is operatively coupled to the fifth connector portion of the second multi-limb connector for selective movement into and out of the first multi-limb connector through the fourth connector portion of the second multi-limb connector, and wherein the gas delivery catheter is selectively moveable between a first position in which at least a portion of the gas delivery catheter is disposed within the first multi-limb connector and a standby position in which substantially no portion of the gas delivery catheter is disposed within the first multi-limb connector; and
   a suction catheter having a second diameter, wherein the suction catheter is operatively coupled to the sixth connector portion of the second multi-limb connector for selective movement into and out of the first multi-limb connector through the fourth connector portion of the second multi-limb connector, and wherein the suction catheter is selectively moveable between a first position in which at least a portion of the suction catheter is disposed within the first multi-limb connector and a standby position in which substantially no portion of the suction catheter is disposed within the first multi-limb connector,
   wherein an inside diameter of the fourth connector portion of the second multi-limb catheter is less than an outside diameter of the gas delivery catheter and an outside diameter of the suction catheter combined, so that only one of the gas delivery catheter and the suction catheter is capable of passing through the fourth connector portion into the first multi-limb connector at any one time due to one of the gas delivery catheter and the suction catheter located within the fourth connector portion substantially blocking the other of the gas delivery catheter and the suction catheter from entering the fourth connector portion.

2. An adapter assembly according to claim 1, wherein the second connector portion, the fifth connector portion, and the sixth connector portion are all disposed in a common plane.

3. An adapter assembly according to claim 1, wherein the fifth connector portion and the sixth connector portion merge at the fourth connector portion.

4. An adapter assembly according to claim 1, further comprising at least one of:
   (a) a first swivel member provided at the second connector portion to permit rotational movement of the first multi-limb connector relative to a endotracheal tube; and
   (b) a second swivel member provided at the first connector portion to permit rotational movement of the first multi-limb connector relative to a breathing gas tube coupled to a ventilator.

5. An adapter assembly according to claim 1, further comprising at least one of:
   (a) a first clamp member operatively coupled to the fifth connector portion that, upon being actuated, prevents axial movement of the gas delivery catheter relative to the fifth connector portion; and
   (b) a second clamp member operatively coupled to the sixth connector portion that, upon being actuated, prevents axial movement of the suction catheter relative to the sixth connector portion.

6. An adapter assembly according to claim 1, further comprising at least one of:
   (a) a first indicator disposed on the gas delivery catheter for indicating whether the gas delivery catheter is located in the first multi-limb connector; and
   (b) a second indicator disposed on the suction catheter for indicating whether the suction catheter is located in the first multi-limb connector.

7. An adapter assembly according to claim 1, further comprising at least one of:
   (a) a first plurality of location marks disposed on the gas delivery catheter; and
   (b) a second plurality of location marks disposed on the suction catheter.

8. An adapter assembly according to claim 7, further comprising a viewing window defined in the first multi-limb connector so as to allow visual inspection of a portion of the gas delivery catheter and the suction catheter located within the first multi-limb connector.

9. An adapter assembly according to claim 8, wherein the viewing window includes a magnifying element.

10. A method of selectively delivering gas to and suctioning a substance from a patient, comprising:
   (a) providing an adapter assembly for connection to a proximal end of an endotracheal tube, the adapter assembly comprising:
      a first multi-limb connector having a first connector portion adapted to be coupled to a ventilator, a second connector portion adapted to be connected to an endotracheal tube, and a third connector portion;
      a second multi-limb connector having a fourth connector portion adapted to be immovably coupled to the third connector portion of the first multi-limb connector; a fifth connector portion, and a sixth connector portion;
      a gas delivery catheter having a first diameter, wherein the gas delivery catheter is operatively coupled to the fifth connector portion of the second multi-limb connector for selective movement into and out of the first multi-limb connector through the fourth connector portion of the second multi-limb connector, and wherein the gas delivery catheter is selectively moveable between a first position in which at least a portion of the gas delivery catheter is disposed within the first multi-limb connector and a standby position in which substantially no portion of the gas delivery catheter is disposed within the first multi-limb connector; and a suction catheter having a second diameter, wherein the suction catheter is operatively coupled to the sixth connector portion of the second multi-limb connector for selective movement into and out of the first multi-limb connector through the fourth connector portion of the second multi-limb connector, and wherein the suction catheter is selectively moveable between a first position in which at least a portion of the suction catheter is disposed within the first multi-limb connector and a standby position in which substantially no portion of the suction catheter is disposed within the first multi-limb connector, wherein an inside diameter of the fourth connector portion of the second multi-limb catheter is less than an outside diameter of the gas delivery catheter and an outside diameter of the suction catheter combined, so that only one of the gas delivery catheter and the suction catheter is capable of passing through the fourth connector portion into the first multi-limb connector at any one time due to one of the gas delivery catheter and the suction catheter located within the fourth connector portion substantially blocking the other of the gas delivery catheter and the suction catheter from entering the fourth connector portion (b) moving the gas delivery catheter from the standby position to the first position so that the gas delivery catheter passes through the fourth connector portion and at least a portion of the gas delivery catheter is disposed within the first multi-limb connector, and wherein the gas delivery catheter occupies a majority of the inside diameter of the fourth connector portion responsive to being in the first position so as to substantially block the suction catheter from entering the first multi-limb connector; and (c) moving the suction catheter from the standby position to the first position so that the suction catheter passes through the fourth connector portion and at least a portion of the suction catheter is disposed within the first multi-limb connector, and wherein the suction catheter occupies a majority of the inside diameter of the fourth connector portion responsive to being in the first position so as to substantially block the gas delivery catheter from entering the first multi-limb connector.

11. A method according to claim 10, further comprising actuating a clamping member to prevent axial movement of at least one of the gas delivery catheter and the suction catheter relative to an associated fifth connector portion and sixth connector portion.

12. A method according to claim 10, further comprising viewing at least one of a first indicator disposed on the gas delivery catheter for indicating whether the gas delivery catheter is located in the first multi-limb connector and a second indicator disposed on the suction catheter for indicating whether the suction catheter is located in the first multi-limb connector.

13. A method according to claim 10, further comprising viewing at least one of a first plurality of location marks disposed on the gas delivery catheter and a second plurality of location marks disposed on the suction catheter.

14. A method according to claim 13, wherein the viewing step includes viewing the location marks through a viewing window disposed on of a side wall and a second end of the main cylindrical tube.

* * * * *